United States Patent [19]

Do Coutto Filho et al.

[11] Patent Number: 5,780,699
[45] Date of Patent: Jul. 14, 1998

[54] SYNTHETIC BASESTOCKS AND PROCESS FOR PRODUCING SAME

[75] Inventors: Odyr Do Coutto Filho; Noemi Tatizawa, both of Rio de Janeiro, Brazil

[73] Assignee: Petroleo Brasileiro S.A.-Petrobras, Rio de Janeiro, Brazil

[21] Appl. No.: 701,535

[22] Filed: Aug. 26, 1996

Related U.S. Application Data

[63] Continuation of Ser. No. 355,346, Dec. 12, 1994, abandoned.

[30] Foreign Application Priority Data

Jan. 12, 1994 [BR] Brazil .................. 9400079-4

[51] Int. Cl.⁶ .................. C07C 2/08; C07C 2/74
[52] U.S. Cl. .................. 585/532; 585/530; 585/255
[58] Field of Search .................. 585/532, 530, 585/255, 324

[56] References Cited

U.S. PATENT DOCUMENTS

| | | | |
|---|---|---|---|
| 3,639,366 | 2/1972 | Broca et al. | 260/82 |
| 3,987,123 | 10/1976 | Lepert | 526/76 |
| 4,017,553 | 4/1977 | Cesca et al. | 585/532 |
| 4,113,790 | 9/1978 | Cesca et al. | 585/532 |
| 4,167,534 | 9/1979 | Petrillo et al. | 585/532 |
| 4,172,855 | 10/1979 | Shubkin et al. | 585/532 |
| 4,400,565 | 8/1983 | Darden et al. | . |
| 4,420,646 | 12/1983 | Darden et al. | 585/10 |
| 4,992,183 | 2/1991 | Beimesch et al. | . |
| 5,030,791 | 7/1991 | Sanderson et al. | 585/530 |
| 5,382,739 | 1/1995 | Atkins et al. | 585/530 |

FOREIGN PATENT DOCUMENTS

| | | |
|---|---|---|
| 8304576 | 8/1983 | Brazil . |
| 8304576 | 4/1985 | Brazil . |

Primary Examiner—Glenn Caldarola
Assistant Examiner—Thuan D. Dang
Attorney, Agent, or Firm—Sughrue, Mion, Zinn, Macpeak & Seas, PLLC

[57] ABSTRACT

A process is described for the production of synthetic basestocks from an alpha-olefin feedstock with carbon number in the range $C_7$–$C_{30}$ the feedstock having origin in an ethylene polymerization process, the process comprising contacting the feedstock with a solid or soluble cationic $AlCl_3$ catalyst. After separation and distilling out of the light fraction of the oligomer, a basestock of excellent viscometric, rheological and thermal stability properties is obtained. The basestocks so obtained are also described.

11 Claims, 1 Drawing Sheet

SYNTHETIC BASESTOCKS AND PROCESS FOR PRODUCING SAME

This is a Continuation of application Ser. No. 08/355,346 filed Dec. 12, 1994, abandoned.

BACKGROUND OF THE INVENTION

1. Filed of the Invention

The present invention deals with a process for producing synthetic basestocks through the oligomerization of a $C_7$–$C_{30}$ alpha-olefin feedstock.

More specifically, the present invention deals with a process for producing synthetic basestocks through the oligomerization of an alpha-olefin feedstock which is the by-product of a Ziegler ethylene polymerization in the presence of a cationic initiator. The process still comprises distilling out the light fraction with hydrogenation of the basestock product in order to increase its stability. The present invention relates also to the synthetic basestocks obtained through the process of the invention.

2. Prior Art

In order to withstand the increasing working temperature of engines caused by their reduced size intended to save weight and fuel, basestocks of increasing thermal stability are required. Compared to basestocks of petroleum origin, synthetic basestocks show excellent thermo-oxidative stability, low volatility and high viscosity index, which means better lubricating capacity, with longer intervals for replacement, with less product vaporization between changes. The longer useful life and thus longer chance intervals render synthetic basestocks more interesting also from the environmental point of view.

Synthetic basestocks are obtained via oligomerization of internal and terminal olefins, chiefly alpha-olefins only, to produce a mixture of dimers, trimers, tetramers and pentamers. Oligomers are hydrogenated in order to increase stability.

In view of their commercial interest, oligomerization of internal as well as terminal olefins as a means of producing synthetic basestocks has been the object of many patents.

U.S. Pat. No. 4,400,565 describes a synthetic basestock which is prepared through the oligomerization of a feedstock made up of alpha- and internal olefins, the internal olefins making up more than 50 weight % of the mixture, in the presence of $BF_3$ as catalyst and a cationic exchange resin under oligomerization conditions. The number of carbons of alpha- and internal olefins of the feedstock are the same or nearly the same, while in the internal olefins the double bond is statistically distributed.

U.S. Pat. No. 4,420,646 teaches a process for obtaining basestock through the oligomerization of alpha- and internal olefins which are made to react with $BF_3$ and a protonic promoter, wherein the portion of internal olefins is more than 50 and less than 99 weight % of the mixture, preferably between 50 and 90 weight % of the mixture. The feedstock is made up of olefins in the range $C_9$–$C_{24}$, preferably between $C_{13}$–$C_{15}$. Because the internal olefins are prepared by the dehydrogenation of paraffins, which produces a statistical or thermodynamical distribution of the internal double bond, in the internal olefins the double bond is situated in a statistical position.

U.S. Pat. No. 4,992,183 describes basestocks which are oligomers in the range $C_{30}$–$C_{72+}$ derived from decene-1, which are hydrogenated and compounded with additives in order to obtain motor oils meeting the API requirements. It is alleged that the oils dispense with the use of viscosity index improvers, which is interesting to avoid degradation of the additive in the high shear conditions present in the motors.

It is found that the documents cited in the prior art use as feedstock highly valuable synthetic olefins, the feedstock itself being a synthesis product or either a pure monomer such as decene-1, thus rendering the production processes of these basestocks rather expensive.

Thus, one objective of the present invention is a process for producing synthetic basestocks from a low grade, low worth olefin feedstock normally used as a fuel oil and which is the by-product of an ethylene polymerization reaction, the feedstock being made up exclusively of alpha-olefins, the reaction being effected in the presence of a cationic catalyst, preferably a widely known catalyst such as $AlCl_3$.

Another objective is a process for producing synthetic basestocks of high thermal stability and high viscosity index from an alpha-olefin feedstock which is the by-product of an ethylene polymerization reaction, and which are useful for automotive motors, gears, electrical insulation and greases among other uses. These basestocks can be used in admixture with petroleum basestocks and in these cases can be used as a substitute for viscosity index improvers.

Another objective is the production of synthetic basestocks of viscosity index higher than 120 and pour point lower than $-33°$ C. by effecting the inventive process on the $250°$ C.- cut of the so-called High Boiler (HB) olefin feedstock, which is a by-product of an ethylene polymerization reaction. Basestocks are thus produced which are kept fluid at low temperatures ($<-33°$ C.) while showing low viscosity changes over a wide temperature range. This makes their use possible under extreme temperature situations.

An additional objective is to produce synthetic basestocks wherein the reacted alpha-olefin feedstock when submitted to a separation of the products boiling between $250°$ C.–$350°$ C./1 atm yields different grades of synthetic basestocks which are useful for different end uses.

BEST MODE

Figure 1:
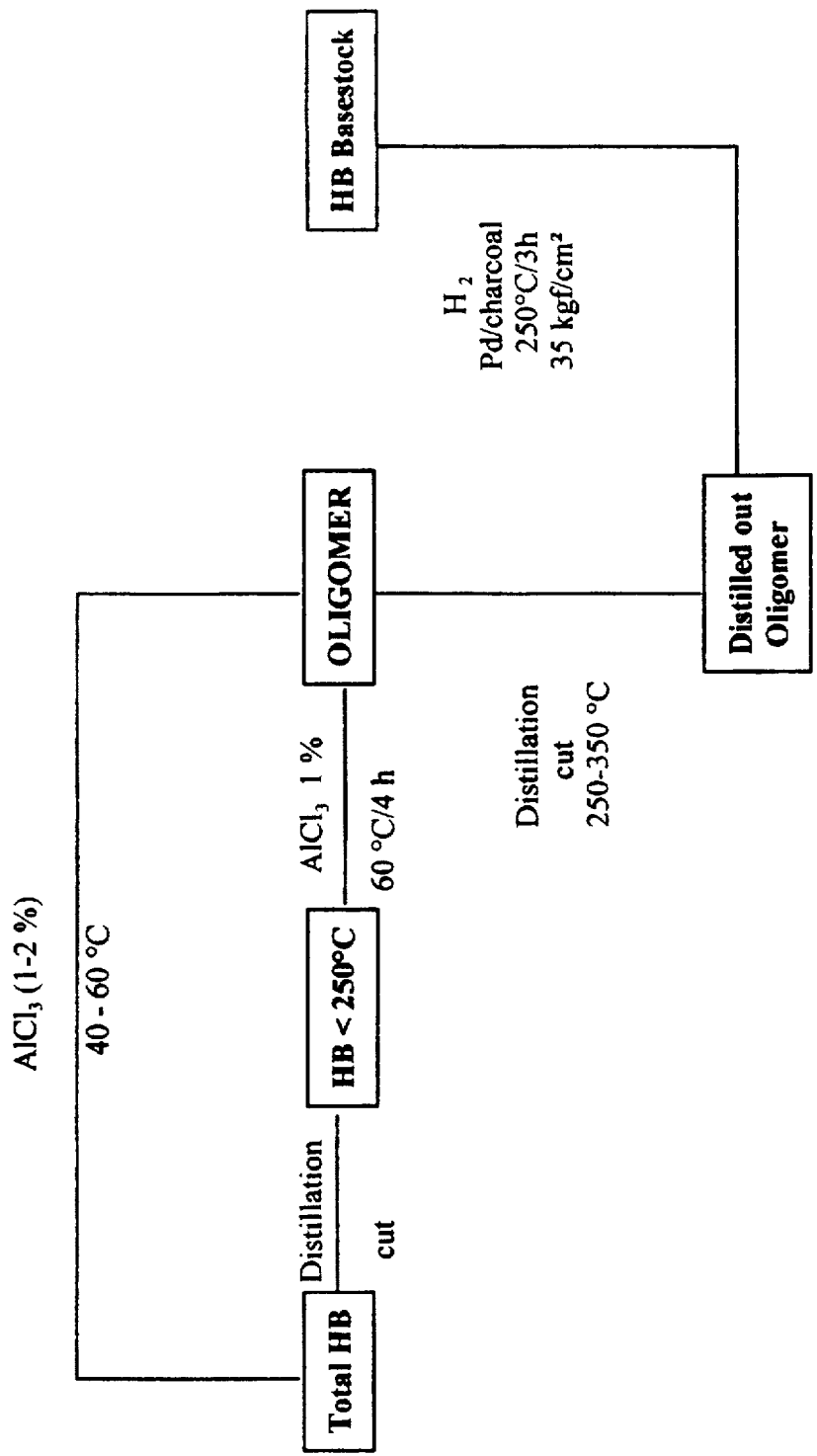
FIG. 1 is a simplified flowsheet of the process for producing synthetic basestocks according to the present invention, which shows the different reaction and product possibilities according to the use of either the total HB feedstock (without cuts) or the $250°$ C. cut.

In the best mode of the present inventions, the preferred feedstock is made up of the olefinic portion "High Boiler" (HB) which is the by-product of the ethylene polymerization according to the Ziegler-Natta process used by the Polialden Petroquimica S.A. company, Bahia, Brazil. This fraction contains a mixture of alpha-olefins in the range $C_7$–$C_{30}$, of average olefin content between 30 and 60%. The feedstocks to be submitted to the process contain between 3.0 to 15.0% of terminal olefinic carbon, between 9.0 and 45.0% of branched saturated carbon and between 45.0 and 85.0% of paraffinic aliphatic saturated carbon. A simulated distillation of the feedstock indicates IBP between $60°$–$150°$ C. and FBP between $410°$ and $500°$ C.

The best mode of the invention uses the $250°$C. cut.

The catalyst system is a cationic system based on $AlCl_3$ either as powder or in soluble form, according to two initiation modes:

a) Acid Friedel-Crafts system with solid $AlCl_3$, the cation source being $H_2O$, according to the scheme below:

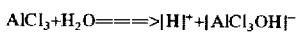

wherein $H^+$ is the real initiator.

b) Stable carbonium ion system with $AlCl_3$/alpha,alpha,alpha-trichlorotoluene/toluene, according to the scheme

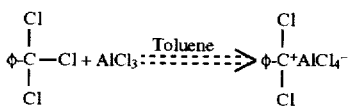

The catalyst systems show high production output (nearly 100%), and at the same time they influence the percentual distribution of branched and paraffinic carbon. Thus, the solid $AlCl_3$ system as compared to the soluble system produces a higher percentage of branched carbon as well as of the $C_{30}^+$ oligomer, the boiling point of which is >500° C.

Another interesting point is that the initiator system based on soluble $AlCl_3$ yields nearly 1 to 4% aromatic carbon, due to the incorporation of carbocationic species.

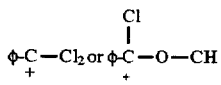

to the oligomer.

The catalyst preparation is as follows:

a) solid $AlCl_3$ $AlCl_3$ is used as such. The active species is produced through the contact with residual water molecules from the feedstock.

b) soluble $AlCl_3$

The preparation of soluble $AlCl_3$ follows the procedure of the Brazilian patent PI BR 8304576, whereby $AlCl_3$ is diluted in an aromatic hydrocarbon such as toluene, benzene, etc. and then is contacted with a polyhalogenated aromatic solvent such as alpha, alpha, alpha-trichlorotoluene ($\alpha, \alpha, \alpha,$ -TCT) at molar ratios of $AlCl_3$/TCT between 0.5:1 and 1.5:1, the lower limit being a function of the onset of $AlCl_3$ solubility. The so obtained mixture shows two phases, the active phase being the more dense and colored in dark red. The chosen catalyst amount is added to the reactor by means of a syringe.

The general procedure to prepare the inventive oligomers is as follows:

The desired oligomer synthesis is effected in a pressurized reactor and under nitrogen atmosphere. Between 500 and 800 ml of alpha-olefin HB feedstock are introduced in the reactor, the desired temperature and agitation speed being maintained with the aid of a monitor coupled to the reaction unit. The necessary amount of solid or soluble $AlCl_3$ initiator is then added, this amount being between 0.5 and 5% based on the reaction mass, preferably between 1 and 2%.

The oligomerization reaction can be effected in the range between 40°–90° C. preferably between 40°–60° C.

At the end of the reaction which can last for 3 to 5 hours, the reaction liquid is washed under agitation in 500 ml of a 10% aqueous NaOH solution followed by several (4 to 6) washings with 200–250 ml of water.

The light fraction is then distilled out from the reaction liquid; the distillation cut can be effected in various temperatures, between 250° and 350° C., according to the desired basestock grade. The cut is effected under reduced pressure between 50 and 5 mm Hg.

Finally the oligomer product is hydrogenated to increase stability by saturating residual double bonds. Hydrogenation is effected in the presence of 1–2 wt % of a hydrogenation catalyst based on nickel or palladium, under pressure of 20–40 kgf/cm$^2$ $H_2$ and temperature of 180°–210° C. under agitation. Reaction time varies between 3 and 4 hours, after what the system is cooled to room temperature. Pressure in the reactor is then alleviated and the hydrogenated oligomer is filtrated in order to separate the suspended catalyst. Reaction yield is nearly 100%.

The oligomer of the present invention, produced according to the flowsheet of FIG. 1 shows excellent characteristics of viscosity index, low volatility, low pour point and high flash point as will be demonstrated below.

The present invention will be now illustrated by the following examples, which should not be construed as limiting.

EXAMPLES 1 TO 6

These examples illustrate the process for producing synthetic basestock while using 1% wt based on the feed of solid $AlCl_3$ as catalyst, at temperatures between 25° and 164° C.$^+$, from 700 ml of HB feedstock. $C^{13}$ NMR results of analysis of the kinds of carbons (olefinic, paraffinic and branched) as well as the simulated distillation are listed on TABLE 1 below.

TABLE 1

| Example | Temp. (°C.) | C$^{13}$ NMR | | | Sim. Dist. | |
| --- | --- | --- | --- | --- | --- | --- |
| | | Co (%) | Cp (%) | Cbr (%) | % distilled | °C. |
| Feedstock | — | 5.7 | 84.7 | 9.8 | IBP | 164 |
| | | | | | 30 | 250 |
| | | | | | 50 | 282 |
| | | | | | FBP | 494 |
| 1 | 50 | 1.8 | 64.5 | 33.7 | 10 | 174 |
| | | | | | 30 | 293 |
| | | | | | 48 | >544 |
| 2 | reflux >164° C. | 1.8 | 64.0 | 34.4 | 10 | 124 |
| | | | | | 30 | 216 |
| | | | | | 35 | >545 |
| 3 | 25 | 1.7 | 62.2 | 36.1 | — | — |
| 4 | 40 | 1.9 | 66.0 | 32.1 | 10 | 173 |
| | | | | | 30 | 285 |
| | | | | | 50 | >500 |
| 5 | 35 | 1.7 | 65.2 | 33.1 | 10 | 173 |
| | | | | | 30 | 285 |
| | | | | | 50 | >500 |
| 6 | 25 | 1.8 | 62.2 | 36.0 | 10 | 173 |
| | | | | | 30 | 285 |
| | | | | | 50 | >500 |

Co = olefinic carbon
Cp = paraffinic, saturated carbon
Cbr = branched saturated carbon In order to establish how varies the distribution of the several kinds of carbon olefinic, paraffinic and saturated branched) throughout an oligomerization reaction typical of the present invention, a reaction was run for 4 hours, using as initiator $AlCl_3$/$H_2O$ at 40° C., 700 ml HB feedstock and 5 g $AlCl_3$. TABLE 2 lists the analysis results by $C^{13}$ NMR.

TABLE 2

| | $^{13}$C NMR (%) | | |
| --- | --- | --- | --- |
| Time (h) | Unsat. Carbon. | Sat. Paraf. Carbon. | Branched sat. Carbon. |
| — | 5.7 | 84.7 | 9.8 |
| ¼ | 4.2 | 68.7 | 27.2 |

TABLE 2-continued

| | $^{13}$C NMR (%) | | |
|---|---|---|---|
| Time (h) | Unsat. Carbon. | Sat. Paraf. Carbon. | Branched sat. Carbon. |
| ½ | 3.0 | 66.8 | 30.2 |
| ¾ | 2.8 | 67.2 | 29.8 |
| 1 | 2.3 | 67.4 | 30.3 |
| 1½ | 2.9 | 64.6 | 32.5 |
| 2 | 2.7 | 66.3 | 31.0 |
| 3 | 2.2 | 65.8 | 31.9 |
| 4 | 1.8 | 62.2 | 36.0 |

From Table 2 it can be seen that the content of branched saturated carbon increases quickly from 9.8% to 27.2% in the first 15 minutes of the reaction, reaching 36% at the end of four hours. Thus, the lowering of the double bond content consequent to its consumption during oligomerization is accompanied by a branching reaction in the oligomer, the paraffinic saturated carbon being reduced accordingly.

As described hereinbefore, the following step of the process comprises distilling out the light fraction which contains the non-reacted portion of the HB feedstock by effecting a cut at a temperature between 250° and 350° C., preferably under reduced pressure.

The oligomers of Examples 4, 5 and 6 were distilled out using a cut at 140° C./50 mm Hg (250° C./1 atm).

The next step is the hydrogenation of the oligomer fraction in order to increase stability. The hydrogenation is effected by means of a Ni-Raney, Ni, Ni-Co-Cr or Ni-kieselguhr, Pd/charcoal, etc. catalyst.

TABLE 3 below lists the hydrogenation results for Examples 4, 5 and 6 in the presence of a commercial Pd/charcoal catalyst.

TABLE 3

| Sample | Catalyst | % cat. in reaction | React. Cond. | % Co | % Cp | % C br | C br/ C p |
|---|---|---|---|---|---|---|---|
| Total HB | Harshaw Ni (57%) | 1.0 | T = 120° C. P = 7.5 kgf/cm² time = 6.5 h | 0.1 | 79.3 | 20.6 | 0.5 |
| Ex. 4 (120) | Degussa Pd/charcoal (0.15%) | 1.5 | T = 200° C. P = 35 kgf/cm² time = 3 h | 0.1 | 59.5 | 40.4 | 0.7 |
| Ex. 5 | Degussa Pd/charcoal (0.15%) | 1.0 | T = 200° C. P = 35 kgf/cm² time = 3 h | zero | 59.2 | 40.8 | 0.7 |
| Ex. 6 | Degussa Pd/charcoal (0.15%) | 1.5 | T = 200° C. P = 35 kgf/cm² time = 3 h | zero | 59.0 | 41.0 | 0.7 |

Co = olefinic carbon
Cp = paraffinic, saturated carbon
C br = branched, saturated carbon Hydrogenations favor isomerization reactions, as shown by the increase of the Cbr/Cp ratio from nearly 0.5 to 0.7.

As mentioned before, the hydrogenation activity is high, nearly 100%, as demonstrated by the low contents of double bond (0–0.1%) in the hydrogenated product.

The oligomer of Example 6 was analyzed by simulated distillation in order to observe its modification after distillation of the light fraction and hydrogenation, according to TABLE 4 below.

TABLE 4

| Ex. 6 Distilled out and hydrogenated | | Ex. 6 | |
|---|---|---|---|
| % | °C. | % | °C. |
| beginning | 215 | beginning | 118 |
| 3 | 250 | 10 | 173 |
| 24 | 502 | 22 | 250 |
| 26 | 534 | 30 | 287 |
| 74 | >534 | 47 | 494 |
| | | 50 | >536 |

Data from TABLE 4 show that the percentage of carbons higher than $C_{30}$(b.p.>530° C.) increased from 50 to 74% thus demonstrating the efficacy of the distillation cut. Note that only 3% of oligomer boiling below 250° C. could be found, while in the as-produced (that is, not distilled out) oligomer this figure reached 22%.

The distilled out and hydrogenated oligomer of Example 6 was analyzed by means of Gel Permeation Chromatography (GPC) in order to assess the molecular weights. The values are Mw=1680 and Mn=1300 with polidispersity 1.28. For the sake of comparison, commercial basestocks Hydrogenated Medium Neutral (HMN) and Light Neutral (LN) showed the following values:

| | | Mw | Mn | Polidispersity |
|---|---|---|---|---|
| basestock | HMN | 553 | 514 | 1.07 |
| | LN | 625 | 519 | 1.07 |

Therefore, it can be found that the molecular weight of the oligomer of Example 6 is two to three times higher than that of the cited commercial basestocks, for similar structures.

Finally, physical properties of the basestocks of Examples 4, 5 and 6 distilled out and hydrogenated (4 DH, 5 DH and 6 DH) were measured. Data are listed on TABLE 5 below.

TABLE 5

| Properties | Whole Product | Ex. 4 DH | Ex. 5 DH | Ex. 6 DH | LN | MN | Decene-1 Oligomer Oil |
|---|---|---|---|---|---|---|---|
| Kinematic viscosity at | 12.5 | 30.7 | 40.7 | 49.9 | 30.3 | 59.9 | 29.0 |

TABLE 5-continued

| Properties | Whole Product | Ex. 4 DH | Ex. 5 DH | Ex. 6 DH | LN | MN | Decene-1 Oligomer Oil |
|---|---|---|---|---|---|---|---|
| 40° C. (cst) Kinematic viscosity at 40° C. (cst) | 3.8 | 6.8 | 8.3 | 9.7 | 5.0 | 7.5 | 5.7 |
| Dynamic viscosity −18° C. (cp) | <500 | 11000 | — | — | — | — | 1010 |
| Viscosity Index | 226 | 189 | 185 | 186 | 96 | 95 | 140 |
| Pour point (°C.) | −18 | −9 | −6 | +3 | −3 | −6 | −54 |
| Flash point (°C.) | — | — | 168 | — | 226 | 244 | 235 |

LN = Light Neutral Commercial basestock
MN = Hydrogenated Medium Neutral basestock
DH = Distilled Hydrogenated Data from TABLE 3 lead to the conclusion that the distillation-hydrogenation process, with withdrawal of the light portion and eventual isomerization causes an increase in the kinematic viscosity, lowers the viscosity index V.I. and increases the pour point, if one compares Example 4 Distilled out and Hydrogenated (Ex. 4 DH), Example 5 Distilled out and Hydrogenated (Ex. 5 DH) and Example 6 Distilled out and Hydrogenated (Ex 6 DH) with the whole product of 4 hours of reaction on TABLE 2, without distillation nor hydrogenation.

Besides the viscosity index of the basestocks from the HB oligomers are high; they are higher than those of mineral basestocks LN and MN as well as higher than those of the 1-decene oligomers of the state-of-the-art showing similar kinematic viscosity.

EXAMPLES 7 TO 11

An alpha-olefin HB sample which contained 11.2% of olefinic carbon was submitted to the inventive process designed to produce a basestock. Solid $AlCl_3$ as well as $AlCl_3$/alpha, alpha, alpha-TCT/Toluene catalysts were employed. The analysis through $C^{13}$ NMR and simulated distillation is listed on TABLE 6 below. After the oligomerization reactions the products were submitted to a distillation cut under reduced pressure at 150° C./5 mm Hg (300° C./1 atm) in order to separate the lighter fractions. Hydrogenation yield was 100% (values of olefinic carbon between 0–0.1%, as measured by $C^{13}$ NMR) in the presence of 1.5 wt % of commercial catalyst Pd/charcoal (0.15% Pd), at 200° C., 35 kgf/cm², 3 hours.

TABLE 6

| Example | Temp. (°C.) | Cat. (%) | $C^{13}$ NMR C p | C br | Co | Sim. Distillation % dist. | T (°C.) |
|---|---|---|---|---|---|---|---|
| HB FEED-STOCK | — | — | 46.2 | 42.7 | 11.2 | IBP | 66 |
|  |  |  |  |  |  | 30 | 161 |
|  |  |  |  |  |  | 50 | 176 |
|  |  |  |  |  |  | 75 | 252 |
|  |  |  |  |  |  | FBP | 460 |
| 7 | 40 | Solid AlCl₃ (3) | 52.1 | 46.6 | 1.3 | IBP | 71 |
|  |  |  |  |  |  | 30 | 224 |
|  |  |  |  |  |  | 50 | 479 |
|  |  |  |  |  |  | 50 | >500 |
| 8 | 40 | Solid AlCl₃ (1) | 50.1 | 48.1 | 1.8 | IBP | 71 |
|  |  |  |  |  |  | 30 | 251 |
|  |  |  |  |  |  | 50 | 493 |
|  |  |  |  |  |  | 50 | >500 |
| 9 | zero | Solid AlCl₃ (1) | 51.3 | 43.1 | 5.6 | IBP | 61 |
|  |  |  |  |  |  | 30 | 192 |
|  |  |  |  |  |  | 50 | 297 |
|  |  |  |  |  |  | 40 | >500 |
| 10 | 40 | Solid Soluble (1) | 53 | 42.7 | 4.3 | IBP | 61 |
|  |  |  |  |  |  | 30 | 173 |
|  |  |  |  |  |  | 50 | 286 |
|  |  |  |  |  |  | 35 | >500 |
| 11 | 40 | Solid Soluble (2) | 50.3 | 47.9 | 1.8 | IBP | 61 |
|  |  |  |  |  |  | 30 | 214 |
|  |  |  |  |  |  | 50 | 457 |
|  |  |  |  |  |  | 48 | >500 |
| 12 | 40 | Solid AlCl₃ (1) | — | — | — | IBP | 97 |
|  |  |  |  |  |  | 30 | 256 |
|  |  |  |  |  |  | 50 | 453 |
|  |  |  |  |  |  | 45 | >500 |
| 13 | 40 | Solid Soluble (1) | — | — | — | IBP | 64 |
|  |  |  |  |  |  | 30 | 157 |
|  |  |  |  |  |  | 50 | 218 |
|  |  |  |  |  |  | 75 | 393 |
|  |  |  |  |  |  | 20 | >500 |
| 14 | 60 | Solid AlCl₃ (1) | 0.5 | 49.3 | 50.2 | IBP | 94 |
|  |  |  |  |  |  | 30 | 251 |
|  |  |  |  |  |  | 51 | >500 |

For Examples 7 to 11, after distillation and hydrogenation, the number average molecular weight Mn, weight average molecular weight Mw and polydispersity PD were ascertained by GPC and osmometry, according to data listed on TABLE 7 below.

TABLE 7

| EXAMPLE | Mn | Mw | PD | Mn osmometric |
|---|---|---|---|---|
| 7 DH | 1142 | 1.994 | 1.75 | 1080 |
| 8 DH | 1046 | 1.570 | 1.50 | 986 |
| 9 DH | 1966 | 3.103 | 1.58 | 1860 |
| 10 DH | 980 | 1.469 | 1.50 | 927 |
| 11 DH | 908 | 1.338 | 1.47 | 860 |

Comparative Example 1

A few properties of the inventive synthetic basestocks were compared to those of mineral basestocks and those of decene-1 oligomer basestock. TABLE 8 below lists results of thermal stability as measured by Thermogravimetric analysis at 250° C. at heating rate 10° C./minute.

TABLE 8

| Sample | % weight loss at $N_2$ atm | at $O_2$ atm |
|---|---|---|
| Light Neutral Min. Basestock | 22.0 | 20.0 |
| Hydrogenated Light Neutral Min. Basestock | 7.0 | 7.0 |
| Synthetic Basestock HB 754 | 3.5 | 3.5 |
| decene-1 oligomer basestock | 5.0 | 6.0 | while TABLE 9 below lists a few properties of the synthetic basestocks of Examples 7 to 11 and those of a decene-1 oligomer basestock.

TABLE 9

| PROPERTIES | Ex. 7 | Ex. 8 | Ex. 9 | Ex. 10 | Ex. 11 | DECENE-1 OLIGOMER BASESTOCK |
|---|---|---|---|---|---|---|
| Flash point, °C. | 234 | 252 | 100 | 230 | — | 166 |
| Viscosity at 40°, cSt | 231.8 | 197.3 | 17.58 | 167.3 | 163.3 | 55.48 |
| Viscosity at 100°, cSt | 24.76 | 21.53 | 4.565 | 19.48 | 18.88 | 9.955 |
| Viscosity Index | 135 | 130 | 189 | 134 | 131 | 168 |
| Pour Point, °C. | 0 | −3 | +9 | −6 | −6 | <−30 |

EXAMPLE 15

This Example illustrates the preferred mode of the present invention since it embodies a synthetic basestock of excellent viscosity index and pour point, which are comparable to those obtained from processes which employ starting feedstocks of higher initial worth than the feedstock of the present process. In this mode, the present process uses the 250° C. of the HB petrochemical portion, this cut representing $C_7$–$C_{15}$ olefins. Reaction is run at 60° C., 1 wt % solid $AlCl_3$ and 4 hours reaction time, after what a cut at 143° C./10 mm Hg (2800° C./1 atm) is isolated, which is hydrogenated with Degussa Pd/charcoal (0.15%) catalyst at 200° C., 35 kgf/cm² for 3 hours. $C^{13}$ NMR analysis showed a product of zero % olefinic carbon. Analysis figures for the basestock demonstrate the excellence of the inventive process:

Kinematic viscosity at 40° C. (ASTM D 445) (cSt) 122.0
Kinematic viscosity at 100° C. (ASTM D 445) (cSt) 15.40
Pour point, °C. <−33
Viscosity index 131
Flash Point °C. 220

Molecular weights determined according to the usual analytical techniques were as follows: Mw=1341; Mn=860 while the polydispersity was 1.56. The low pour point is credited to the probably more branched molecular structure which causes that the basestock keeps its flowing properties at low temperatures without solidifying.

In case the 250° C.⁻ cut is used, the 250° C.⁺ makes up a basestock fraction of high viscosity which can be used as an additive for other applications.

Comparative Example 2

Under the same reaction conditions of Example 15, the whole HB portion was submitted to the inventive process, with the results below:

Kinematic viscosity at 40° C. 130.5
Kinematic viscosity at 100° C. 16.35
Flash point, °C. 220
Pour point, °C. +3
Viscosity index 134
Molecular weight measurements indicated Mw=1659, Mn=1173 and polydispersity 1.41.

We claim:

1. A process for producing a synthetic basestock having a flash point of from 150° to 280° C., a kinematic viscosity at 40° C. of from 10 to 250 cSt, a kinematic viscosity at 100° C. of from 3 to 30 cSt, a viscosity index of from 120 to 200 and a pour point of from 0° to less than −33° C., by oligomerizing an α-olefin feedstock, wherein the process comprises the steps of:

(a) contacting an $AlCl_3$ cationic catalyst with an α-olefin feedstock, so as to oligomerize said feedstock, wherein said α-olefin feedstock comprises a mixture of α-olefin containing 7 to 30 carbon atoms, an olefin content of from 30 to 60 volume % and a terminal olefin carbon content of from 3.0 to 15 mole % and wherein said $AlCl_3$ cationic catalyst is a soluble catalyst complex of $AlCl_3$/α, α, α-trichlorotoluene dissolved in toluene, wherein the relative amount of $AlCl_3$ to α, α, α-trichlorotoluene is from 0.5:1 to 1.2:1;

(b) distilling out a light fraction cut under reduced pressure from the resulting product of step (a);

(c) contacting the light fraction cut of step (b) with a hydrogenation catalyst so as to hydrogenate the light fraction cut; and (d) recovering the resulting synthetic basestock from step (c).

2. The process according to claim 1, wherein the α-olefin feedstock of step (a) is produced by ethylene polymerization using a Ziegler-Natta process, and wherein distilling in step (b) occurs at an initial boiling point of from 60° to 150° C. and a final boiling point of from 410° to 500° C.

3. The process according to claim 1, wherein distilling in step (b) occurs at an initial boiling point of 60° C. and a final boiling point of 250° C.

4. The process according to claim 1, wherein the $AlCl_3$ cationic catalyst is solid $AlCl_3$, and is employed in an amount of from 0.5 to 5 weight % based on the α-olefin feedstock.

5. The process according to claim 1, wherein step (a) is carried out at a temperature of 25° C., and a reflux pressure of from 0.3 to 10 kgf/cm² under an inert atmosphere, for 3 to 5 hours.

6. The process according to claim 1, wherein the light fraction cut is distilled out at from 250° to 350° C./1 atm, or at a reduced pressure and a temperature which would correspond to from 250° to 350° C./1 atm.

7. The process according to claim 1, wherein the hydrogenation catalyst is employed in an amount from 1.0 to 2.0 weight % based on the α-olefin feedstock, and is selected from the group consisting of Ni, Pd/$Al_2O_3$ and Pd/charcoal, and wherein the hydrogenation in step (c) is carried out at a temperature of from 120° to 210° C., and a pressure of from 20 to 40 kgf/cm² $H_2$, for 3 to 7 hours.

8. A synthetic basestock having a flash point of from 150° to 280° C., a kinematic viscosity at 40° C. of from 10 to 250 cSt, a kinematic viscosity at 100° C. of from 3 to 30 cSt, a viscosity index of from 120 to 200 and a pour point of from 0° to −33° C., wherein the synthetic basestock is prepared by a process comprising the steps of:

(a) contacting an $AlCl_3$ cationic catalyst with an α-olefin feedstock, so as to oligomerize said feedstock, wherein said α-olefin feedstock comprises a mixture of α-olefin containing 7 to 30 carbon atoms, an olefin content of from 30 to 60 volume % and a terminal olefin carbon content of from 3.0 to 15 mole % and wherein said $AlCl_3$ cationic catalyst is a soluble catalyst complex of $AlCl_3/\alpha, \alpha, \alpha$-trichlorotoluene dissolved in toluene, wherein the relative amount of $AlCl_3$ to $\alpha, \alpha, \alpha$-trichlorotoluene is from 0.5:1 to 1.2:1;

(b) distilling out a light fraction cut under reduced pressure from the resulting product of step (a);

(c) contacting the light fraction cut of step (b) with a hydrogenation catalyst so as to hydrogenate the light fraction cut; and (d) recovering the resulting synthetic basestock from step (c).

9. The synthetic basestock according to claim 8, wherein said feedstock has a weight loss of less than 4%, as measured in a thermogravimetric analysis test at 250° C.

10. A process for producing a synthetic basestock having a flash point of from 150° to 280° C., a kinematic viscosity at 40° C. of from 10 to 250 cSt, a kinematic viscosity at 100° C. of from 3 to 30 cSt, a viscosity index of from 120 to 200 and a pour point of from 0° to −33° C., by oligomerizing an α-olefin feedstock, wherein the process comprises the steps of:

(a) contacting an $AlCl_3$ cationic catalyst with an α-olefin feedstock, so as to oligomerize said α-olefin feedstock, wherein said α-olefin feedstock comprises a mixture of α-olefin containing 7 to 30 carbon atoms, an olefin content of from 30 to 60 volume %, between 3.0 and 15.0 moles of terminal carbon, between 9.0 and 45.0 mole % branched saturated carbon and between 45.0 and 85.9 mole % of paraffinic aliphatic saturated carbon, and wherein said $AlCl_3$ cationic catalyst is a soluble catalyst complex of $AlCl_3/\alpha, \alpha, \alpha$-trichlorotoluene dissolved in toluene, wherein the relative amount of $AlCl_3$ to $\alpha, \alpha, \alpha$-trichlorotoluene is from 0.5:1 to 1.2:1;

(b) distilling out a light fraction cut under reduced pressure from the resulting product of step (a);

(c) contacting the light fraction cut of step (b) with a hydrogenation catalyst so as to hydrogenate the light fraction cut; and (d) recovering the resulting synthetic basestock from step (c).

11. A synthetic basestock having a flash point of from 150° to 280° C., a kinematic viscosity at 40° C. of from 10 to 250 cSt, a kinematic viscosity at 100° C. of from 3 to 30 cSt, a viscosity index of from 120 to 200 and a pour point of from 0° to −33° C., wherein the synthetic basestock is prepared by the process of claim 10.

* * * * *

UNITED STATES PATENT AND TRADEMARK OFFICE
CERTIFICATE OF CORRECTION

PATENT NO. : 5,780,699
DATED : July 14, 1998
INVENTOR(S) : Odyr Do Coutto Filho, et. al.

It is certified that error appears in the above-identified patent and that said Letters Patent is hereby corrected as shown below:

Column 8, Table 6, in the column labeled "Cat. (%)", for each of the Samples 10, 11, and 13, the language, "Solid Soluble"

should read -- Soluble $AlCl_3$ --.

Signed and Sealed this

Ninth Day of February, 1999

Attest:

Attesting Officer

Acting Commissioner of Patents and Trademarks